(12) United States Patent
Sharma et al.

(10) Patent No.: US 9,388,178 B2
(45) Date of Patent: Jul. 12, 2016

(54) PROCESS FOR THE PREPARATION OF MOXIFLOXACIN HYDROCHLORIDE

(71) Applicant: Mankind Research Centre c/o Mankind Research Centre (A Division of Mankind Pharma Ltd.), New Delhi (IN)

(72) Inventors: Harish Sharma, Haryana (IN); Bhuwan Bhaskar, Haryana (IN); Anil Kumar, Haryana (IN)

(73) Assignee: Mankind Research Centre (IN)

( * ) Notice: Subject to any disclaimer, the term of this patent is extended or adjusted under 35 U.S.C. 154(b) by 0 days.

(21) Appl. No.: 14/648,129

(22) PCT Filed: Nov. 21, 2013

(86) PCT No.: PCT/IB2013/060299
§ 371 (c)(1),
(2) Date: May 28, 2015

(87) PCT Pub. No.: WO2014/087292
PCT Pub. Date: Jun. 12, 2014

(65) Prior Publication Data
US 2015/0307490 A1    Oct. 29, 2015

(30) Foreign Application Priority Data

Dec. 4, 2012 (IN) .......................... 3712/DEL/2012

(51) Int. Cl.
*C07D 471/04* (2006.01)
(52) U.S. Cl.
CPC .................... *C07D 471/04* (2013.01)
(58) Field of Classification Search
CPC ..................................... C07D 471/04
See application file for complete search history.

(56) References Cited

U.S. PATENT DOCUMENTS

| 5,157,117 | A | * | 10/1992 | Takagi | ............... C07F 5/04 540/541 |
| 5,849,752 | A | | 12/1998 | Grunenberg et al. | |
| 7,732,612 | B2 | * | 6/2010 | Grant | ............ C07D 215/56 546/156 |
| 2006/0264635 | A1 | | 11/2006 | Satyanarayana et al. | |

FOREIGN PATENT DOCUMENTS

| CN | 102276603 A | 12/2011 |
| CN | 102617622 A | 8/2012 |
| CN | 102276603 B | 10/2012 |
| EP | 0350733 B1 | 1/1990 |
| EP | 0550903 A1 | 7/1993 |
| EP | 0657448 B1 | 6/1995 |
| IN | 518/DEL/2010 A | 9/2011 |
| WO | 2008059223 A2 | 5/2008 |
| WO | 2010052726 A1 | 5/2010 |

OTHER PUBLICATIONS

Zhang, Bioorg & Med Chem Lett, VOl 21 (2011), 928-931.*
International Bureau of WIPO, International Preliminary Report on Patentablity for International Application No. PCT/IB2013/060299, Jun. 18, 2015, 9 pages.

* cited by examiner

*Primary Examiner* — D M Seaman
(74) *Attorney, Agent, or Firm* — Fish & Tsang LLP

(57) ABSTRACT

The present invention relates to an improved and industriously advantageous process by means of providing coupling/condensing of wet mass of (1-cyclopropyl-6,7-difluoro-8-methoxy-4-oxo-1,4-dihydro-3-quinoline carboxylic acid-$O^3,O^4$)bis(acyloxy-O)borate with (S,S)-2,8-diazabicyclo[4.3.0]nonane to give 1-cyclopropyl-7-[S,S]-2,8-diazabicyclo-[4.3.0]non-8-yl)-6-fluoro-1,4-dihydro-8-methoxy-4-oxo-3-quinoline carboxylic acid hydrochloride (Moxifloxacin hydrochloride) of Formula-I with high purity.

Formula-I

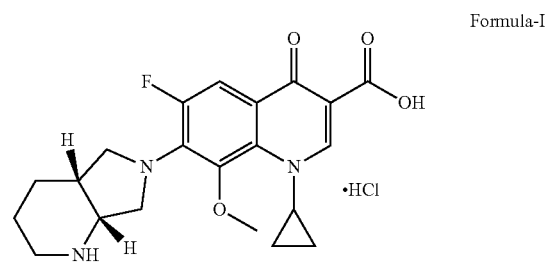

11 Claims, No Drawings

PROCESS FOR THE PREPARATION OF MOXIFLOXACIN HYDROCHLORIDE

FIELD OF THE INVENTION

The invention, in general, relates to a process for the preparation of 1-cyclopropyl-7-[S,S]-2,8-diazabicyclo-[4.3.0]non-8-yl)-6-fluoro-1,4-dihydro-8-methoxy-4-oxo-3-quinoline carboxylic acid hydrochloride (Moxifloxacin hydrochloride) with high purity.

More particularly, the present invention provides an industrially applicable and economical process by means of providing coupling of wet mass of (1-cyclopropyl-6,7-difluoro-8-methoxy-4-oxo-1,4-dihydro-3-quinoline carboxylic acid-$O^3,O^4$)bis(acyloxy-O)borate with (S,S)-2,8-diazabicyclo[4.3.0]nonane to give 1-cyclopropyl-7-[S,S]-2,8-diazabicyclo-[4.3.0]non-8-yl)-6-fluoro-1,4-dihydro-8-methoxy-4-oxo-3-quinoline carboxylic acid hydrochloride (Moxifloxacin hydrochloride) of Formula-I with high yield and purity.

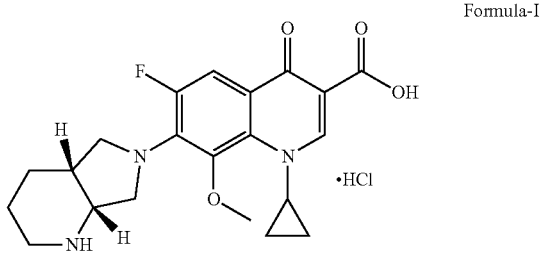 [SMILES: COc1c(N2C[C@H]3CCCN[C@H]3C2)c(F)cc2c(=O)c(C(=O)O)cn(C3CC3)c12 ; Cl]

Formula-I

BACKGROUND OF THE INVENTION

Moxifloxacin Hydrochloride chemically known as 1-cyclopropyl-7-[S,S]-2,8-diazabicyclo-[4.3.0]non-8-yl)-6-fluoro-1,4-dihydro-8-methoxy-4-oxo-3-quinoline carboxylic acid hydrochloride is a synthetic fluoroquinoline broad spectrum antibacterial particularly against Gram-positive bacteria and is known from EP 350,733 and EP 550,903 with following chemical structure.

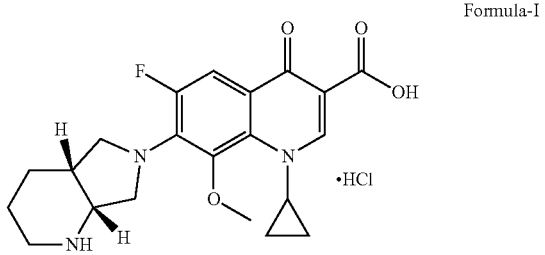 [SMILES: COc1c(N2C[C@H]3CCCN[C@H]3C2)c(F)cc2c(=O)c(C(=O)O)cn(C3CC3)c12 ; Cl]

Formula-I

Moxifloxacin has activity against Gram-negative and Gram-positive microorganisms, including *Streptococus pneumonia, Staphylococcus aureus, Pseudomonas aeruginosa, Haemophilus influenza, Haemophilus parainfluenzae* and *Moraxella catarrhalis* and the activity shown to be unaffected by β-lactamases. Moxifloxacin is used to treat number of infections including endocarditis meningitis, tuberculosis, respiratory tract infections, anthrax and cellulitis.

US Application 20060264635 discloses process for the preparation of Moxifloxacin hydrochloride by using intermediate (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(acyloxy-O)borate. The disclosure further refers to the preparation of above said intermediate by condensing dried (1-cyclopropyl-6,7-difluoro-8-methoxy-4-oxo-1,4-dihydro-3-quinoline carboxylic acid-$O^3,O^4$)bis(acyloxy-O)borate with (S,S)-2,8-diazabicyclo [4.3.0]nonane in solvents like Dimethyl sulfoxide (DMSO), Dimethyl formamide (DMF), Acetonitrile (ACN) or ethanol and base under heating conditions, which is then hydrolysed to get Moxifloxacin hydrochloride pseudohydrate followed by conversion to Moxifloxacin hydrochloride monohydrate by treating with HCl in ethanol.

The major drawback of the above mentioned process is that multiple isolation steps are required to get desired Moxifloxacin hydrochloride monohydrate, which ultimately results into increase in production cost.

PCT Application WO2008059223 discloses the process for the preparation of Moxifloxacin hydrochloride by condensing dried mass of (1-cyclopropyl-6,7-difluoro-8-methoxy-4-oxo-1,4-dihydro-3-quinoline carboxylic acid-$O^3,O^4$)bis(propyloxy-O)borate with (S,S)-2,8-diazabicyclo[4.3.0]nonane in an organic solvent such as Acetonitrile (ACN) or n-butanol at higher temperatures to obtain intermediate (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(propyloxy-O)borate which is then hydrolysed using Hydrochloric acid (HCl) in methanol to get Moxifloxacin hydrochloride. Above mentioned process further refers the isolation of Moxifloxacin hydrochloride through acid base treatment which is being performed twice to get 'C' form of Moxifloxacin hydrochloride.

Here, condensation reaction requires higher temperature conditions which lead to the degradation of the compound and hence decreases the overall yield of the process. Moreover, there is involved an extra step of acid base treatment making process lengthy and unsuitable to employ at industrial scale.

The European Patent No's EP 350,733; EP 550,903 and EP 657,448 disclose the preparation of moxifloxacin hydrochloride involving the condensation of dried 1-cyclopropyl-6,7-difluoro-8-methoxy-4-oxo-1,4-dihydro-3-quinoline carboxylic acid or its esters with (S,S)-2,8-diazabicyclo[4.3.0] nonane in presence of base and its conversion to hydrochloride at higher temperatures leading to the formation of desired moxifloxacin along with its positional isomer namely 1-cyclopropyl-6-[S,S]-2,8-diazabicyclo-[4.3.0]non-8-yl)-7-fluoro-1,4-dihydro-8-methoxy-4-oxo-3-quinoline carboxylic acid of Formula I-A as a major impurity.

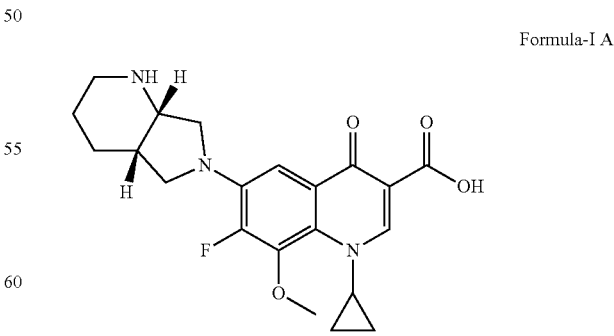

Formula-I A

The separation of side impurities and positional isomer in above said process entails tedious purification processes which results into lower yields thereby increasing cost of production.

U.S. Pat. No. 5,157,117 discloses (1-cyclopropyl-6,7-difluoro-8-methoxy-4-oxo-1,4-dihydro-3-quinoline carboxylic acid-$O^3$,$O^4$)bis(acyloxy-O)borate and process of its preparation by reacting ethyl-1-cyclopropyl-6,7-difluoro-8-methoxy-4-oxo-1,4-dihydro-3-quinoline carboxylate with boric acid and acetic anhydride in presence of zinc chloride and its conversion to Moxifloxacin hydrochloride.

The known forms of Moxifloxacin hydrochloride are the anhydrous and monohydrate. U.S. Pat. No. 5,849,752 discloses the monohydrate of Moxifloxacin hydrochloride and its preparation by treating the anhydrous crystalline form with ethanol/water mixture.

PCT Application WO2010052726 discloses preparation of Moxifloxacin hydrochloride by condensing dried mass of (1-cyclopropyl-6,7-difluoro-8-methoxy-4-oxo-1,4-dihydro-3-quinoline carboxylic acid-$O^3$,$O^4$)bis(acyloxy-O)borate with (S,S)-2,8-diazabicyclo[4.3.0]nonane in presence of solvent like toluene and base at reflux conditions. Similarly, Chinese Patent No. CN 102,276,603 discloses preparation of Moxifloxacin hydrochloride using dried mass of acyloxy boron complex and condensing it with (S,S)-2,8-diazabicyclo[4.3.0]nonane in presence of solvent like Acetonitrile (ACN) and base at reflux conditions.

The drawback of above said process is that condensation reaction is performed at reflux conditions which results into decomposition of boron complex, (1-cyclopropyl-6,7-difluoro-8-methoxy-4-oxo-1,4-dihydro-3-quinoline carboxylic acid-$O^3$,$O^4$)bis(acyloxy-O)borate resulting into formation of unwanted side products and hence loss in the overall yield.

Indian Patent No. IN 2010DE00518 discloses the preparation of Moxifloxacin hydrochloride by condensing boron complex, (1-cyclopropyl-6,7-difluoro-8-methoxy-4-oxo-1, 4-dihydro-3-quinoline carboxylic acid-$O^3$,$O^4$)bis(acyloxy-O)borate with (S,S)-2,8-diazabicyclo[4.3.0]nonane in water using organic base at 45-50° C.

It is observed that the isolated Moxifloxacin hydrochloride is not of desired purity. To get Moxifloxacin hydrochloride of pharmacopeial grade, further crystallization in methanol and water is required. However the further purification results into massive loss in the yield of the desired product making process unsuitable at commercial scale production.

Chinese Patent No. CN 102,617,622 reveals preparation of moxifloxacin hydrochloride by condensing dried (1-cyclopropyl-6,7-difluoro-8-methoxy-4-oxo-1,4-dihydro-3-quinoline carboxylic acid-$O^3$,$O^4$)bis(acyloxy-O)borate with (S,S)-2,8-diazabicyclo[4.3.0]nonane in Acetonitrile (ACN) using Triethyl amine (TEA) as a base at room temperature.

In the prior art, the acyloxy borate complex namely (1-cyclopropyl-6,7-difluoro-8-methoxy-4-oxo-1,4-dihydro-3-quinoline carboxylic acid-$O^3$,$O^4$)bis(acyloxy-O)borate is firstly dried under thermal conditions before using it for the condensation reaction. It is being observed that the acyloxy borate complex is thermally unstable compound and drying of the same requires critical parameters which are difficult to maintain at plant scale. Also, the drying of acyloxy boron compound is time consuming process, requiring approximately 24-32 hours of constant heating.

The processes disclosed in the prior art involve not only time-consuming steps but also multiple isolations, tedious work-ups and time-consuming purification processes, which results into wastage of material, thus making process lengthy, low yielding and uneconomical at commercial scale production.

Therefore, it is long felt need of the industry to provide high yielding and cost effective processes for the production of Moxifloxacin hydrochloride.

OBJECT AND SUMMARY OF THE INVENTION

It is the principle object of the present invention to improve upon the shortcomings in the prior art by providing an improved process for preparing Moxifloxacin hydrochloride of Formula-I, which is employed for the treatment of endocarditis meningitis, tuberculosis, respiratory tract infections, anthrax and cellulitis.

It is another object of the present invention to provide a commercially viable, economical and environment friendly process for preparing Moxifloxacin hydrochloride of Formula-I, wherein the process employs minimal purification steps and wastage of material.

It is yet another object of the present invention, to provide a process for preparation of Moxifloxacin hydrochloride of Pharmacopoeial grade with high yield at industrial scale employing user friendly, cost efficient raw material and solvents.

Accordingly, the present invention provides an improved process for the preparation of Moxifloxacin hydrochloride represented by Formula-I

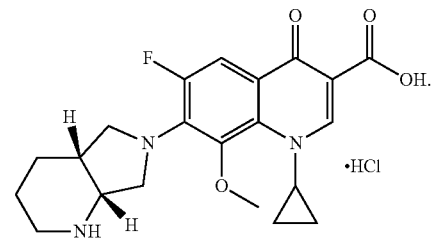

Formula-I

In one embodiment, the present invention provides a process for the preparation of moxifloxacin hydrochloride, wherein the process comprises the steps of:

(i) condensing a compound of Formula-II,

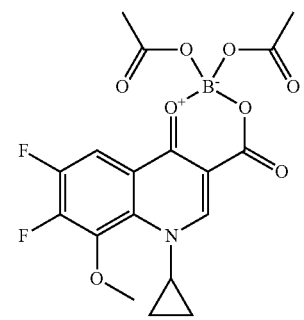

Formula-II with a compound of Formula-III,

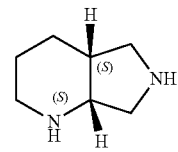

Formula-III in presence of a base in a solvent system to produce an intermediate compound of Formula-IV,

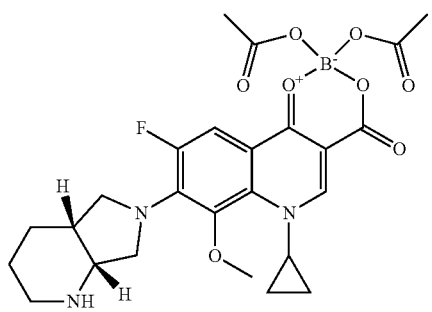

Formula-IV (ii) optionally isolating the compound of Formula-IV, and
(iii) hydrolysing the compound of Formula-IV to form moxifloxacin hydrochloride.

In this process, the compound of Formula-II has a moisture content of about 10 to about 50%, and the solvent system comprises an organic solvent and water.

It is an object of the present invention to make use of Compound of Formula-II as a wet cake or wet mass with moisture content of 10-50%, preferably 25-45% of moisture by weight.

It is another object of the invention, that the solvent system used in the process comprises an organic solvent and water. The water in the said solvent system is in the ratio of 5-60% by weight of organic solvent.

In this invention, the organic solvents used in the process are selected from the group of alcohols, nitriles, esters, ketones, hydrocarbons, chlorinated solvents, amides, sulfoxides and ethers. Preferably, the solvents used are selected from isopropyl alcohol, ethanol, methanol, acetonitrile, ethyl acetate, toluene, xylene, methylene dichloride, chloroform, dimethyl sulfoxide, N-methyl pyrrolidine, dimethyl formamide or a mixture thereof. In the most preferred embodiment, the organic solvent is selected from acetonitrile, isopropyl alcohol, methanol, ethanol, methylene dichloride or a mixture thereof.

In one embodiment, the reaction of the present process is carried out at a temperature of 5-40° C.

The base in the process is selected from an organic or an inorganic base. The organic base is selected from triethyl amine (TEA), diisopropyl ethyl amine (DIPEA), dimethyl aniline, diisopropyl amine (DIPA), 1,8-Diazabicyclo[5.4.0]undec-7-ene (DBU) or a mixture thereof. The inorganic base is selected from carbonates, bicarbonates, hydroxides, alkoxides, hydrides, or a mixture thereof. Preferably, the inorganic base is selected from potassium carbonate, sodium carbonate, cesium carbonate, potassium bicarbonate, sodium bicarbonate, sodium hydroxide, potassium hydroxide, sodium methoxide, potassium tert-butoxide, sodium hydride or a mixture thereof.

In one embodiment, the compound of Formula-IV is hydrolysed/reacted with an acid in the presence of an alcohol, to form moxifloxacin hydrochloride. The alcohol in the process is selected from the group of $C_1$-$C_4$ alcohols.

The improved process of the present invention for the preparation of 1-cyclopropyl-7-[S,S]-2,8-diazabicyclo-[4.3.0]non-8-yl)-6-fluoro-1,4-dihydro-8-methoxy-4-oxo-3-quino line carboxylic acid hydrochloride (moxifloxacin hydrochloride) of Formula-I, provides moxifloxacin hydrochloride with a purity of above 99.7%.

The above and other objects of the present invention are further attained and supported by the following embodiments described herein. However, the described embodiments are in accordance with the best mode of practice and the scope of the invention is not restricted to the described embodiments herein after.

DETAILED DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

The steps of a method may be providing more details that are pertinent to understanding the embodiments of the present invention and so as not to obscure the disclosure with details that will be readily apparent to those of ordinary skill in the art having benefit of the description herein.

Further characteristics and advantages of the process according to the invention will result from the description herein below of preferred exemplary embodiments, which are given as indicative and non-limiting examples.

The present invention provides an improved and industrially advantageous process for the preparation of Moxifloxacin hydrochloride of Formula-I.

According to the present invention there is provided an improved method for preparation of Moxifloxacin hydrochloride, with high purity and yield, which is amenable at large scale production.

In accordance to one embodiment of the present invention, the process of preparation of Moxifloxacin hydrochloride represented by Formula-I comprises the steps of:

(i) condensing wet mass of (1-cyclopropyl-6,7-difluoro-8-methoxy-4-oxo-1,4-dihydro-3-quinoline carboxylic acid-$O^3$,$O^4$)bis(acyloxy-O)borate of Formula-II Formula-II

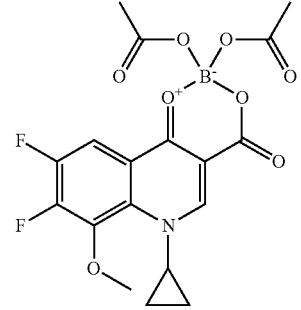

with (S,S)-2,8-diazabicyclo[4.3.0]nonane of Formula-III

Formula-III

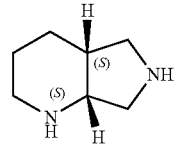

in presence of base in a solvent system to produce intermediate compound, (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3$,$O^4$)bis (acyloxy-O)borate of Formula-IV, said solvent system comprising a mixture of one or more organic solvents with water,

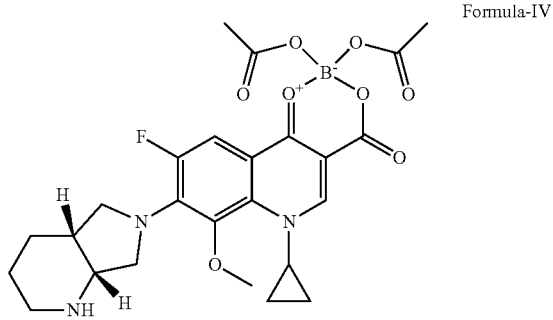

Formula-IV (ii) optionally isolating the intermediate compound of Formula-IV, and
(iii) reacting the intermediate compound of Formula-IV, with acid in alcohol to form moxifloxacin hydrochloride of Formula-I.

In further embodiment of the present invention, the organic solvent is selected from the group of alcohols, nitriles, esters, ketones, hydrocarbons, chlorinated solvents, amides, sulfoxides and ethers. Preferably, the organic solvent is selected from isopropyl alcohol, ethanol, methanol, acetonitrile, ethyl acetate, toluene, xylene, methylene dichloride, chloroform, dimethyl sulfoxide, N-methyl pyrrolidine, dimethyl formamide or a mixture thereof.

In an embodiment, the solvent system comprises an organic solvent and water. The water is provided from the wet mass of compound of Formula-II. In another embodiment, the water in the solvent system is provided by addition of water. The water in the solvent system is in the range of 5-60% by weight of organic solvent.

In another embodiment of the present invention, the reaction is carried out at a low temperature of 15-30° C.

According to one embodiment, the present invention provides a process for the preparation of Moxifloxacin hydrochloride of Formula-I starting from compound of Formula-II. Wet mass of (1-cyclopropyl-6,7-difluoro-8-methoxy-4-oxo-1,4-dihydro-3-quino line carboxylic acid-$O^3,O^4$)bis(acyloxy-O)borate of Formula-II is condensed with (S,S)-2,8-diazabicyclo[4.3.0]nonane of Formula-III in presence of base in a solvent system at low temperature.

The solvent system employed in preparation of Moxifloxacin hydrochloride comprises of one or more organic solvents with water, wherein the organic solvent is selected from the group of alcohols, nitriles, esters, ketones, hydrocarbons, chlorinated solvents, amides, sulfoxides and ethers. Preferably, the organic solvent is selected from isopropyl alcohol, ethanol, methanol, acetonitrile, ethyl acetate, toluene, xylene, methylene dichloride, chloroform, dimethyl sulfoxide, N-methyl pyrrolidine, dimethyl formamide or mixture thereof. Most preferably, organic solvent is selected from acetonitrile, isopropyl alcohol, methanol, ethanol, methylene dichloride or a mixture thereof.

The solvent system comprising organic solvent(s) with water, is prepared in such a way that the % wt of water in the solvent system is 5-60%, preferably 7-40%, which is achieved by maintaining the ratio of % wt of the moisture content of wet cake of the compound of Formula-II and % wt of demineralised water added externally to the solvent system.

The reaction is carried out a temperature range of 5-40° C., preferably 10-25° C.

In the process of present invention, the starting material (1-cyclopropyl-6,7-difluoro-8-methoxy-4-oxo-1,4-dihydro-3-quinoline carboxylic acid-$O^3,O^4$)bis(acyloxy-O)borate of Formula-II can be prepared according to the methods known in the prior art. In contrast to the prior art, the desired compound of Formula-II is isolated as a wet cake with moisture content of 10-50%, preferably 25-45% of moisture by weight. Said wet cake or wet mass of compound of Formula-II is preferably not dried before using it.

In another embodiment of present invention, the base used in preparation of intermediate compound of Formula-IV is an organic or inorganic base. The organic base is selected from the group of aromatic or aliphatic amines like triethyl amine (TEA), diisopropyl ethyl amine (DIPEA), dimethyl aniline, diisopropyl amine (DTPA), 1,8-Diazabicyclo[5.4.0]undec-7-ene (DBU) or a mixture thereof. The inorganic base is selected from the group of carbonates, bicarbonates, hydroxides, alkoxides, and hydrides. Preferably, the inorganic base is selected from potassium carbonate, sodium carbonate, cesium carbonate, potassium bicarbonate, sodium bicarbonate, sodium hydroxide, potassium hydroxide, sodium methoxide, potassium tert-butoxide, sodium hydride or a mixture thereof. Most preferably, triethyl amine is used as a base.

In yet another embodiment of the present invention, the intermediate compound, (4aS-Cis)-(1-cyclopropyl-7-(2,8-diazabicyclo[4.3.0]non-8-yl)-6-fluoro-8-methoxy-4-oxo-1, 4-dihydro-3-quinoline carboxylic acid-$O^3,O^4$)bis(acyloxy-O)borate of Formula-IV may not be isolated and is hydrolysed to give desired Moxifloxacin hydrochloride using acid, such as hydrochloric acid in gaseous, dilute or concentrated form in a solvent such as alcohol selected from ($C_1$-$C_4$) alcohols. One of the preferred alcohols is isopropyl alcohol. In another embodiment, the intermediate compound, (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(acyloxy-O)borate of Formula-IV may be isolated and then hydrolysed to give desired Moxifloxacin hydrochloride.

In accordance with one embodiment of the present invention, the Moxifloxacin hydrochloride is isolated with high purity of 99.7% or above by HPLC and complies with British Pharmacopoeial grade.

Further, the present invention is illustrated in detail by way of the following examples. The examples are given herein for illustration of the invention and are not intended to be limiting thereof.

Experiment 1

Preparation of 1-cyclopropyl-6,7-difluoro-1,4-dihydro-8-methoxy-4-oxo-3-quinoline carboxylic acid-$O^3,O^4$)bis(acetato-O)-borate 86.5 g (0.848 mol) of Acetic anhydride was heated to 80-90° C. and stirred for 90 min followed by addition of 15.5 g (0.254 mol) of boric acid slowly at a temperature range of 80-90° C. Stirred the reaction mass for 90 min and added 50.0 g (0.169 mol) of 1-cyclopropyl-6,7-difluoro-8-methoxy-4-oxo-1,4-dihydro-3-quinoline carboxylic acid. Stirred the reaction mass under heating at 80-90° C. for 60 min. After completion of reaction, cooled the reaction mass to 0° C., added 250 ml of demineralised water at 0-5° C. and stirred for 1 h. Filtration was carried out to obtain 90 g of wet cake of 1-cyclopropyl-6,7-difluoro-1,4-dihydro-8-methoxy-4-oxo- 3-quinoline carboxylic acid-$O^3,O^4$)bis(acetato-O)-borate having 31% of moisture content.

Experiment 2

Preparation of Moxifloxacin Hydrochloride in a Solvent System Comprising of 8.2% Wt of Water and Acetonitrile To the solution of 650 ml of Acetonitrile and 203 g (0.331 mol) of wet cake of 1-cyclopropyl-6,7-difluoro-1,4-dihydro-8-methoxy-4-oxo-3-quinoline carboxylic acid-$O^3,O^4$)bis(acetato-0)-borate (having 31% moisture content) was added 40.8 g (0.323 mol) of [S,S]-2,8-diazabicyclo-[4,3,0]nonane dissolved in 50 ml of acetonitrile at 10-15° C. To the above reaction mass added 33.4 g (0.330 mol) of triethyl amine and stirred at 15-20° C. for 6-8 h. After completion of reaction, distilled the reaction mixture under vacuum at 30° C. followed by addition of 300 ml of isopropyl alcohol at 10-15° C. Adjusted the pH of the reaction mass to 1.0-2.0 with dilute hydrochloric acid and stirred for 6 h. Cooled the reaction mass to 0-5° C. and filtered the solid mass. The crude mass so obtained was crystallized in methanol and water (3:1) to get wet Moxifloxacin hydrochloride, which in turn, was dried under vacuum to get 118 g of Moxifloxacin hydrochloride having purity 99.97% by HPLC.

Experiment 3

Preparation of Moxifloxacin Hydrochloride in a Solvent System Comprising of 8% Wt of Water and Isopropyl Alcohol To the solution of 25 ml of Isopropyl alcohol and 7.14 g (0.0118 mol) of wet cake of 1-cyclopropyl-6,7-difluoro-1,4-dihydro-8-methoxy-4-oxo-3-quinoline carboxylic acid-$O^3$, $O^4$)bis(acetato-0)-borate (having 30% moisture content) was added 1.45 g (0.0115 mol) of [S,S]-2,8-diazabicyclo-[4,3,0]nonane at 10-15° C. To the above reaction mass added 1.19 g (0.011 mol) of triethyl amine and stirred at 15-20° C. for 8 h. After completion of reaction, cooled the reaction mass to 10° C. and adjusted the pH to 1.0-2.0 with dilute hydrochloric acid. Stirred the reaction mixture for 6 h and cooled to 0-5° C. followed by filtration of solid mass. The crude mass so obtained was crystallized in methanol and water (3:1) to get wet Moxifloxacin hydrochloride, which in turn, was dried under vacuum to get 3.9 g of Moxifloxacin hydrochloride having purity 99.8% by HPLC.

Experiment 4

Preparation of Moxifloxacin Hydrochloride in a Solvent System Comprising of 30% Wt of Water and Acetonitrile To the solution of 240 ml of Acetonitrile and 75 ml of demineralised water was added 99 g (0.1614 mol) of wet cake of 1-cyclopropyl-6,7-difluoro-1,4-dihydro-8-methoxy-4-oxo-3-quinoline carboxylic acid-$O^3,O^4$)bis(acetato-0)-borate (having 31% moisture content) followed by addition of 19.8 g (0.157 mol) of [S,S]-2,8-diazabicyclo-[4,3,0]nonane at 10-15° C. To the above reaction mass added 16.2 g (0.160 mol) of triethyl amine and stirred for 6-8 h at 20° C. After completion of reaction, distilled the reaction mixture under vacuum at 30° C. followed by addition of 300 ml of isopropyl alcohol at 10-15° C. and adjusted the pH to 1.0-2.0 with dilute hydrochloric acid. Stirred the reaction mass for 6 h and filtered the solid mass. Dissolved the solid in 250 ml of demineralised water and adjusted the pH to 7.5-8.0 by aq. ammonia followed by addition of 300 ml of methylene dichloride. Stirred the reaction mixture at 25-30° C. for 20 min. Separated the layers and concentrated the organic layer under vacuum to get crude base. Added 300 ml of acetone to the crude base so obtained, adjusted the pH to 1.0-2.0 with dilute hydrochloric acid and stirred at 0-5° C. for 90 min. Filtration was carried out to get wet Moxifloxacin hydrochloride, which in turn, was dried under vacuum to get 50.4 g of Moxifloxacin hydrochloride having purity 99.76% by HPLC.

Experiment 5

Preparation of Moxifloxacin Hydrochloride in a Solvent System Comprising of 20.7% Wt of Water and Acetonitrile To the solution of 20 ml of Acetonitrile and 3 ml of demineralised water was added 7.24 g (0.0118 mol) of wet cake of 1-cyclopropyl-6,7-difluoro-1,4-dihydro-8-methoxy-4-oxo-3-quinoline carboxylic acid-$O^3,O^4$)bis(acetato-O)-borate as obtained in Experiment 1 followed by addition of 1.45 g (0.0115 mol) of [S,S]-2,8-diazabicyclo-[4,3,0]nonane at 10-15° C. To the above reaction mass added 1.19 g (0.0117 mol) of triethyl amine and stirred for 6-8 h at 20° C. After completion of reaction, distilled the reaction mixture under vacuum at 30° C. followed by addition of 30 ml of isopropyl alcohol at 10-15° C. and adjusted the pH to 1.0-2.0 with dilute hydrochloric acid. Stirred the reaction mass for 6 h and filtered the solid mass. Dissolved the solid in 25 ml of demineralised water and adjusted the pH to 7.5-8.0 by aq. ammonia followed by addition of 25 ml of methylene dichloride. Stirred the reaction mixture at 25-30° C. for 20 min. Separated the layers and concentrated the organic layer under vacuum to get crude base. Added 30 ml of acetone to the crude base so obtained, adjusted the pH to 1.0-2.0 with dilute hydrochloric acid and stirred at 0-5° C. for 90 min. Filtration was carried out to get wet Moxifloxacin hydrochloride, which in turn, was dried under vacuum to get 3.9 g of Moxifloxacin hydrochloride having purity 99.97% by HPLC.

Experiment 6

Preparation of Moxifloxacin Hydrochloride in a Solvent System Comprising of 40% Wt of Water and Acetonitrile To the solution of 15 ml of Acetonitrile and 8 ml of demineralised water was added 7.14 g (0.0118 mol) of wet cake of 1-cyclopropyl-6,7-difluoro-1,4-dihydro-8-methoxy-4-oxo-3-quinoline carboxylic acid-$O^3,O^4$)bis(acetato-O)-borate (having 30% moisture content) followed by addition of 1.45 g (0.0115 mol) of [S,S]-2,8-diazabicyclo-[4,3,0]nonane at 10-15° C. and 1.19 g (0.0117 mol) of triethyl amine Pursued the reaction as per Experiment 5 to get 3.6 g of Moxifloxacin hydrochloride having purity 99.78% by HPLC.

Experiment 7

Preparation of Moxifloxacin Hydrochloride in a Solvent System Comprising of 60% Wt of Water and Acetonitrile To the solution of 10 ml of Acetonitrile and 13 ml of demineralised water was added 7.14 g (0.0118 mol) of wet cake of 1-cyclopropyl-6,7-difluoro-1,4-dihydro-8-methoxy- 4-oxo-3-quinoline carboxylic acid-$O^3,O^4$)bis(acetato-O)-borate (with 30% moisture content) followed by addition of 1.45 g (0.0115 mol) of [S,S]-2,8-diazabicyclo-[4,3,0]nonane at 10-15° C. and 1.19 g (0.0117 mol) of triethyl amine Pursued the reaction as per Experiment 5 to get 3.3 g of Moxifloxacin hydrochloride having purity 99.54% by HPLC.

Experiment 8

Preparation of Moxifloxacin Hydrochloride in a Solvent System Comprising of 14% Wt of Water and Isopropyl Alcohol To the solution of 25 ml of Isopropyl alcohol and 2 ml of demineralised water was added 7.14 g (0.0118 mol) of wet cake of 1-cyclopropyl-6,7-difluoro-1,4-dihydro-8-methoxy-4-oxo-3-quinoline carboxylic acid-$O^3,O^4$)bis(acetato-O)-borate (with 30% moisture content) followed by addition of 1.45 g (0.0115 mol) of [S,S]-2,8-diazabicyclo-[4,3,0]nonane at 10-15° C. and 1.19 g (0.0117 mol) of triethyl amine Stirred the reaction mixture for 8 h for 15-20° C. After completion of reaction, cooled the reaction mixture to 5° C. and adjusted the pH to 1.0-2.0 with dilute hydrochloric acid. Stirred the reaction mass for 6 h and filtered the solid mass. Dissolved the solid in 25 ml of demineralised water and adjusted the pH to 7.5-8.0 by aq. ammonia followed by addition of 25 ml of methylene dichloride. Stirred the reaction mixture at 25-30° C. for 20 min. Separated the layers and concentrated the organic layer under vacuum to get crude base. Added 30 ml of acetone to the crude base so obtained, adjusted the pH to 1.0-2.0 with dilute hydrochloric acid and stirred at 0-5° C. for 90 min. Filtration was carried out to get 3.8 g of Moxifloxacin hydrochloride having purity 99.9% by HPLC.

Experiment 9

Preparation of (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(acyloxy-O)borate of Formula-IV in a solvent system comprising of 20% wt of water and Acetonitrile To the solution of 20 ml of Acetonitrile and 3 ml of demineralised water was added 7.24 g (0.0118 mol) of wet cake of 1-cyclopropyl-6,7-difluoro-1,4-dihydro-8-methoxy-4-oxo-3-quinoline carboxylic acid-$O^3,O^4$)bis(acetato-O)-borate as obtained in Experiment 1 followed by addition of 1.45 g (0.0115 mol) of [S,S]-2,8-diazabicyclo-[4,3,0]nonane at 10-15° C. To the above reaction mass was added 1.19 g (0.0117 mol) of triethyl amine and stirred for 6-8 h at 15-20° C. After completion of reaction, distilled the reaction mixture under vacuum at 30° C. followed by addition of 30 ml of isopropyl ether and stirred for 40 min at ambient temperature. Filtration was carried out to get 6.0 g of (4aS-Cis)-(1-cyclopropyl-7-(2,8-diazabicyclo[4.3.0]non-8-yl)-6-fluoro-8-methoxy-4-oxo-1,4-dihydro-3-quinoline carboxylic acid-$O^3,O^4$)bis(acyloxy-O)borate as yellow coloured solid and was followed as such in next step without any purification.

Experiment 10

Preparation of Moxifloxacin Hydrochloride

To 6.0 g (0.0113 mol) of (4aS-Cis)-(1-cyclopropyl-7-(2,8-diazabicyclo[4.3.0]non-8-yl)-6-fluor-8-methoxy-4-oxo-1,4-dihydro-3-quinoline carboxylic acid-$O^3,O^4$)bis(acyloxy-O) borate as obtained in Experiment 9, was added isopropyl alcohol at 10-15° C. and adjusted the pH to 1.0-2.0 with dilute hydrochloric acid. Stirred the reaction mass for 6 h and filtered the solid mass. Dissolved the solid in 25 ml of demineralised water and adjusted the pH to 7.5-8.0 by aq. ammonia followed by addition of 25 ml of methylene dichloride. Stirred the reaction mixture at 25-30° C. for 20 min. Separated the layer and concentrated the organic layer under vacuum to get crude base. Added 30 ml of acetone to the crude base so obtained, adjusted the pH to 1.0-2.0 with dilute hydrochloric acid and stirred at 0-5° C. for 90 min. Filtration was carried out to get wet Moxifloxacin hydrochloride, which in turn, was dried under vacuum to get 3.8 g of Moxifloxacin hydrochloride having purity 99.96% by HPLC.

Experiment 11

Preparation of Moxifloxacin Hydrochloride in a Solvent System Comprising of 14% Wt of Water and Ethyl Acetate To the solution of 25 ml of Ethyl acetate and 2 ml of demineralised water was added 7.14 g (0.0118 mol) of wet cake of 1-cyclopropyl-6,7-difluoro-1,4-dihydro-8-methoxy-4-oxo-3-quinoline carboxylic acid-$O^3,O^4$)bis(acetato-O)-borate (with 30% moisture content) followed by addition of 1.45 g (0.0115 mol) of [S,S]-2,8-diazabicyclo-[4,3,0]nonane at 10-15° C. and 1.19 g (0.0117 mol) of triethyl amine Pursued the reaction as per Experiment 5 to get 2.9 g of Moxifloxacin hydrochloride having purity 99.4% by HPLC.

COMPARATIVE EXAMPLES

Example 1

Preparation of Moxifloxacin Hydrochloride

To the mixture of 12.5 g (0.029 mol) of dry (1-cyclopropyl-6,7-difluoro-1,4-dihydro-8-methoxy-4-oxo-3-quinoline carboxylic acid-$O^3,O^4$)bis(acetato-O)-borate and 4.2 g (0.033 mol) of [S,S]-2,8-diazabicyclo-[4,3,0]nonane in 25 ml of demineralised water was added 6.25 g (0.061 mol) of triethyl amine and stirred under heating at 45-50° C. for 1.0 to 1.5 h. After completion of reaction, reaction was cooled to 25-30° C. followed by addition of 50 ml of methylene dichloride and stirred the reaction mixture for 20 minutes. Separated the two layers and extracted the aqueous layer by dichloromethane (2×12.5 ml). Combined the organic layers and adjusted the pH ton 1.0-1.5 with concentrated hydrochloric acid at 20-25° C. followed by stirring at 20-25° C. for 2 h. The reaction mixture was then filtered and washed with 12.5 ml of chilled dichloromethane and dried the solid so obtained at 60-70° C. to give 8.9 g of Moxifloxacin hydrochloride having purity 99.6% by HPLC. The resulting product was then recrystalised in methanol:water (8:2) to give 3.0 g of moxifloxacin hydrochloride having purity 99.83% by HPLC.

It is observed that the compound obtained before crystallization with purity of 99.6% was not of standard quality. To get product that can be commercialized in market, this crude compound was further crystallized in methanol and water, but colossal drop in the yield of the desired compound was observed on crystallization (only 3.0 g of desired compound was obtained). This indicates that the reaction is not favoured in neat water; and the actual yield of the compound that can be commercially exploited is very low.

Example 2

Preparation of Moxifloxacin Hydrochloride in a Solvent System Comprising Of 80% Wt of Water and Acetonitrile To the solution of 5 ml of Acetonitrile and 18 ml of demineralised water was added 7.14 g (0.0118 mol) of wet cake of 1-cyclopropyl-6,7-difluoro-1,4-dihydro-8-methoxy-4-oxo-3-quinoline carboxylic acid-$O^3$,$O^4$)bis(acetato-O)-borate (having 30% of moisture content) followed by addition of 1.45 g (0.0115 mol) of [S,S]-2,8-diazabicyclo-[4,3,0]nonane at 10-15° C. To the above reaction mass added 1.19 g (0.0117 mol) of triethyl amine and stirred for 6-8 h at 20° C. After completion of reaction, distilled the reaction mixture under vacuum at 30° C. followed by addition of 25 ml of isopropyl alcohol at 10-15° C. and adjusted the pH to 1.0-2.0 with dilute hydrochloric acid. Stirred the reaction mass for 6 h and filtered the solid mass. Dissolved the solid in 25 ml of demineralised water and adjusted the pH to 7.5-8.0 by aq. ammonia followed by addition of 25 ml of methylene dichloride. Stirred the reaction mixture at 25-30° C. for 20 min. Separated the layer and concentrated the organic layer under vacuum to get crude base. Added 25 ml of acetone to the crude base so obtained, adjusted the pH to 1.0-2.0 with dilute hydrochloric acid and stirred at 0-5° C. for 90 min. Filtration was carried out to get wet Moxifloxacin hydrochloride, which in turn, was dried under vacuum to get 2.65 g of Moxifloxacin hydrochloride having purity 99.76% by HPLC.

As the % wt of water is increased in the solvent system, Moxifloxacin-borate complex of Formula-II starts cleaving back to 1-cyclopropyl-6,7-difluoro-8-methoxy-4-oxo-1,4-dihydro-3-quinoline carboxylic acid, increasing the side product formation and making purification process lengthy. It is observed that the increase in % wt of water above 60-65% in the solvent system results in drop in the yield of the Moxifloxacin hydrochloride. Also the compound isolated is not of commercial grade and need further crystallization, which further decreases the overall yield of the reaction, making process unsuitable for commercial scale production.

The above experiments show that in accordance with the teachings of the present invention, the solvent system is prepared in such a way that it contains 5-60% wt of water. Due to the presence of water in the solvent system, there is no need of using high (Laboratory (LR) or Analytical (AR)) grade solvents for performing the reaction. Reaction performed with commercial grade solvents give equally appreciable results which are comparable to that known in the prior art. This aspect of the present invention provides advantages such as (a) considerable cost benefits; (b) making process easier to be performed at commercial scale.

The quantitative yield of the compound of Formula-I is obtained with purity above 99.7%. This is achieved by performing the reaction at low temperature. As no thermal conditions are provided to the reaction mass, degradation of the compound is decreased. This aspect of the present invention not only shoots up the yield but also eases the purification process.

According to the present invention, the process of preparing Moxifloxacin hydrochloride is conducted by using wet cake of (1-cyclopropyl-6,7-difluoro-8-methoxy-4-oxo-1,4-dihydro-3-quinoline carboxylic acid-$O^3$,$O^4$)bis(acyloxy-O) borate of Formula-II. It is being observed that the acyloxy borate complex is thermally unstable compound and drying of the same requires critical parameters which are difficult to maintain at plant scale. Also, the drying of acyloxy boron compound is time consuming process, requiring approximately 24-32 hours of constant heating. Use of wet mass of compound of Formula-II evades wastage of time and material.

We claim:

1. A process for the preparation of moxifloxacin hydrochloride, comprising the steps of:

(i) condensing a compound of Formula-II,

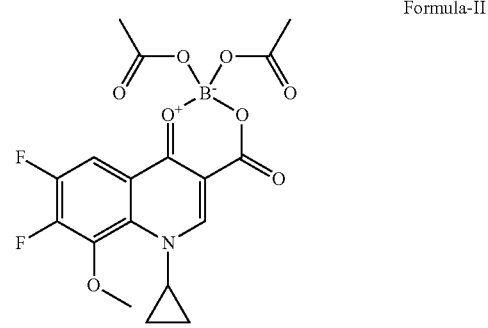 [SMILES: COc1c(F)c(F)cc2c1N(C1CC1)C=C1C(=O)O[B-](OC(C)=O)(OC(C)=O)[O+]=C12]

Formula-II with a compound of Formula-III,

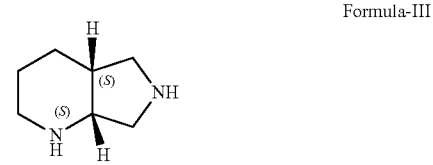

Formula-III in presence of a base in a solvent system to produce an intermediate compound of Formula-IV,

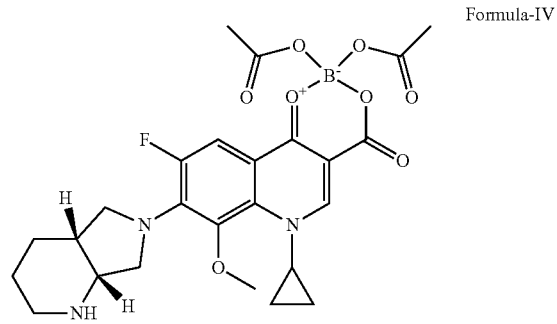 [SMILES: COc1c(N2C[C@H]3CCCN[C@H]3C2)c(F)cc2c1N(C1CC1)C=C1C(=O)O[B-](OC(C)=O)(OC(C)=O)[O+]=C12]

Formula-IV (ii) optionally isolating the compound of Formula-IV, and
   (iii) hydrolysing the compound of Formula-IV to form moxifloxacin hydrochloride,
   wherein the compound of Formula-II has a moisture content of about 10 to about 50%, and the solvent system comprises an organic solvent and water.

2. The process according to claim 1, wherein said organic solvent is selected from alcohols, nitriles, esters, ketones, hydrocarbons, chlorinated solvents, amides, sulfoxides, ethers or a mixture thereof.

3. The process according to claim 2, wherein said organic solvent is selected from acetonitrile, isopropyl alcohol, methanol, ethanol, methylene dichloride or a mixture thereof.

4. The process according to claim 1, wherein the amount of water in the said solvent system is about 5-60% by weight of the organic solvent(s).

5. The process according to claim 1, wherein the reaction of step (i) is carried out at a temperature of 5-40° C.

6. The process according to claim 1, wherein said base is selected from organic or inorganic base.

7. The process according to claim 6, wherein the said organic base is selected from triethyl amine (TEA), diisopropyl ethyl amine (DIPEA), dimethyl aniline, diisopropyl amine (DIPA), 1,8-Diazabicyclo[5.4.0]undec-7-ene (DBU) or a mixture thereof.

8. The process according to claim 6, wherein the said inorganic base is selected from carbonates, bicarbonates, hydroxides, alkoxides, hydrides or a mixture thereof.

9. The process according to claim 8, wherein the said inorganic base is selected from potassium carbonate, sodium carbonate, cesium carbonate, potassium bicarbonate, sodium bicarbonate, sodium hydroxide, potassium hydroxide, sodium methoxide, potassium tert-butoxide, sodium hydride or a mixture thereof.

10. The process according to claim 1, wherein the compound of Formula-IV is hydrolysed with an acid in the presence of an alcohol.

11. The process according to claim 10, wherein said alcohol is selected from the group of $C_1$-$C_4$ alcohols.

\* \* \* \* \*